United States Patent [19]

Lange

[11] 4,320,020
[45] Mar. 16, 1982

[54] ALKYL AMINO PHENOLS AND FUELS AND LUBRICANTS CONTAINING SAME

[75] Inventor: Richard M. Lange, Euclid, Ohio

[73] Assignee: The Lubrizol Corporation, Wickliffe, Ohio

[21] Appl. No.: 249,770

[22] Filed: Apr. 1, 1981

Related U.S. Application Data

[63] Continuation of Ser. No. 676,172, Apr. 12, 1976, abandoned, which is a continuation-in-part of Ser. No. 622,358, Oct. 14, 1975, abandoned.

[51] Int. Cl.$^3$ .............................................. C10M 1/32
[52] U.S. Cl. .................................. 252/51.5 R; 44/58; 44/75; 564/418; 564/419; 564/422; 564/423; 564/439
[58] Field of Search ................ 44/58, 75; 252/51.5 R; 564/418, 419, 422, 423, 439

[56] References Cited

U.S. PATENT DOCUMENTS

| | | | |
|---|---|---|---|
| 2,367,377 | 1/1945 | Reiff et al. ...................... | 252/49.9 X |
| 2,502,436 | 4/1950 | Dawson et al. ...................... | 564/443 |
| 2,831,898 | 4/1958 | Ecke et al. ........................... | 568/781 |
| 2,859,251 | 11/1958 | Linn ..................................... | 568/792 |
| 2,868,844 | 1/1959 | Coffield et al. ..................... | 568/706 |

Primary Examiner—Andrew Metz
Attorney, Agent, or Firm—William H. Pittman; Ronald L. Lyons; John P. Ward

[57] ABSTRACT

Amino phenols of the general formula

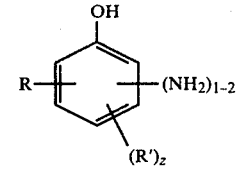

wherein R is a substantially saturated hydrocarbyl substituent having an average of from about 30 to about 750 aliphatic carbon atoms; R' is a substituent selected from the group consisting of lower alkyl, lower alkoxyl, nitro, and halo; and z is 0 or 1, are useful as additives for fuels and lubricants. These amino phenols can be conveniently prepared by nitrating an appropriate hydroxy aromatic compound and reducing the nitro groups to amino groups.

48 Claims, No Drawings

ALKYL AMINO PHENOLS AND FUELS AND LUBRICANTS CONTAINING SAME

REFERENCE TO RELATED APPLICATIONS

This application is a continuation of copending U.S. application Ser. No. 676,172 filed Apr. 12, 1976, now abandoned; which in turn is a continuation-in-part of U.S. application Ser. No. 622,358 filed Oct. 14, 1975 now abandoned. The disclosures of these prior applications are hereby incorporated by reference into this application in their entirety.

Reference is made to my copending U.S. Application Ser. No. 253,830, filed Apr. 13, 1981, entitled "Amino Phenols Useful as Additives for Fuels and Lubricants".

The nitro phenols described herein and the process for reducing such nitro phenols with hydrazine also referred to herein are not part of my invention, but rather are the inventions of Kirk Emerson Davis, described in copending U.S. Application Ser. No. 095,290, filed Nov. 19, 1979 and copending U.S. Application Ser. No. 191,195, filed Sept. 26, 1980.

BACKGROUND OF THE INVENTION (1) Field of the Invention

This invention relates to amino phenols useful as additives in lubricants based on oils of lubricating viscosity and normally liquid fuels. More particularly, it relates to amino phenols having a hydrocarbyl group of at least about 30 aliphatic carbon atoms.

(2) Prior Art

U.S. Pat. No. 2,197,835 describes the formation of metal salts of aromatic amines, said amines being formed by nitration followed by reduction of wax-substituted, hydroxyaromatic hydrocarbons. These metal salts can be incorporated in mineral oils to depress their pour points and increase their viscosity indices.

U.S. Pat. Nos. 2,502,708 and 2,571,092 both disclose the nitration and subsequent hydrogenation to an amine of cardanol. This amino cardanol is said to be useful as an anti-oxidant for mineral oils, fats and petroleum oils. Cardanol, also known as anacardol, is also said to be a mixture of 3-pentadecylphenol, 3-(8'-pentadecenyl)phenol, 3-(8':11'-pentadecadienyl)phenol and 3-(8:11:14'-pentadecatrienyl)phenol. Formulae presented in both the 2,571,092 and 2,502,708 Patents as well as the chemical literature (see the Dictionary of Organic Compounds, Vol. 1, Oxford University Press, N.Y., 1965, page 229) show that the $C_{15}$ substituent in cardanol is meta to the hydroxy group.

U.S. Pat. No. 2,859,251 discloses the alkylation of ortho-, para-, and meta-amino phenols with olefin polymers having from 6 to 18 carbon atoms per molecule in the presence of a catalytic complex formed by mixing hydrogen fluoride with boron trifluoride and an iron group metal fluoride. The 2,853,251 patent fails to disclose whether the alkyl groups in the product mixture are bonded to carbon, nitrogen, and/or oxygen atoms.

General Background

The improvement of the performance characteristics of lubricants based on oils of lubricating viscosity (e.g., oils and greases) and normally liquid fuels though the use of additives has been known for several decades. Still, in these days of growing material shortages, spiralling equipment replacement costs, increasing fuel and lubricant costs, and environmental consciousness, the search for new, effective, alternate lubricant and fuel additives continues unabated.

Objects

Therefore, it is an object of this invention to provide novel additive compositions that will impart useful and desirable properties to oil-based lubricants and normally liquid fuels containing said additive compositions.

It is a further object of this invention to provide novel concentrates, lubricants and fuels containing the amino phenols of this invention.

Other objects will be apparent to those skilled in the art upon review of the present specification.

SUMMARY OF THE INVENTION

This invention comprises amino phenols of the formula

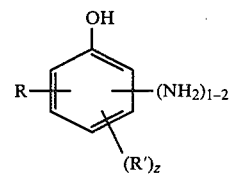

Formula I wherein R is a substantially saturated hydrocarbyl substituent having an average of from about 30 to about 750 aliphatic carbon atoms; R' is a substituent selected from the group consisting of lower alkyl, lower alkoxyl, nitro, and halo; and z is 0 or 1.

Lubricants based on oils of lubricating viscosity, normally liquid fuels and additive concentrates containing the above-described amino phenols are also embodiments of this invention.

DESCRIPTION OF THE INVENTION

The amino phenols of the present invention contain, directly bonded to a benzene ring, a substantially saturated monovalent hydrocarbyl substituent R of from about 30 to about 750 aliphatic carbon atoms. Usually R has at least 50 carbon atoms. Typically R is an alkyl or alkenyl group. Usually R is located ortho or para to the hydroxyl group on the benzene ring.

Generally, the R substituent is made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, 1-octene, etc. Typically, these olefins are 1-monoolefins. The R group can also be derived from the halogenated (e.g., chlorinated or brominated) analogs of such homo- or interpolymers. The R group can, however, be made from other sources, such as monomeric high molecular weight alkenes (e.g., 1-tetracontene) and chlorinated analogs, hydrochlorinated analogs, brominated analogs, and hydrobrominated analogs thereof, aliphatic petroleum fractions, particularly paraffin waxes and cracked and chlorinated and brominated analogs thereof, white oils, synthetic alkenes such as those produced by the Ziegler-Natta process (e.g., poly(ethylene) greases) and other sources known to those skilled in the art. Any unsaturation in the R group can be substantially reduced or eliminated by hydrogenation according to procedures known in the art. Thus the R group is substantially saturated and therefore contains no more than one carbon-to-carbon double or triple bond for every 15 carbon-to-carbon single bonds.

Specific examples of the substantially saturated hydrocarbyl R groups are the following:
- a deca(propylene) group
- a trideca(isobutene) group
- a tetracontanyl group
- a henpentacontanyl group
- a mixture of poly(ethylene/propylene) groups of about 35 to about 70 carbon atoms
- a mixture of the oxidatively or mechanically degraded poly(ethylene/propylene) groups of about 35 to about 70 carbon atoms
- a mixture of poly(propylene/1-hexene) groups of about 80 to about 150 carbon atoms
- a mixture of poly(isobutene) groups having between 40 and 52 carbon atoms
- a mixture of poly(isobutene) groups having an average of 50 to 75 carbon atoms A preferred source of the group R are polybutenes, especially poly(isobutene)s, obtained by polymerization of a C₄ refinery stream having a butene content of 35 to 75 weight percent and isobutene content of 15 to 60 weight percent in the presence of a Lewis acid catalyst such as aluminum trichloride or boron trifluoride. These polybutenes contain predominantly (greater than 80% of total repeat units) isobutene repeating units of the configuration

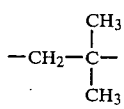

The attachment of the hydrocarbyl group R to the aromatic moiety Ar of the amino phenols of this invention can be accomplished by a number of techniques well known to those skilled in the art. One particularly suitable technique is the Friedel-Crafts reaction, wherein an olefin (e.g., a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride, Methods and conditions for carrying out such reactions are well known to those skilled in the art. See, for example, the discussion in the article entitled, "Alkylation of Phenols" in Kirk-Othmer "Encyclopedia of Chemical Technology", Second Edition, Vol. 1, pages 894-895, Interscience Publishers, a division of John Wiley and Company, N.Y., 1963. Other equally appropriate and convenient techniques for attaching the hydrocarbon-based group R to the aromatic moiety Ar will occur readily to those skilled in the art.

The amino phenols of this invention can optionally contain a lower substituent, R', chosen from the group consisting of lower alkyl (i.e., alkyls of up to 7 carbon atoms), lower alkoxyl, nitro and halo groups. When such R' groups are present, z in Formula I is 1. Usually, however, they are absent and z is 0.

In one embodiment, the amino phenols of this invention have the amino group ortho and the R group para to the phenolic hydroxyl group. This subgenus of amino phenols can be represented by the formula

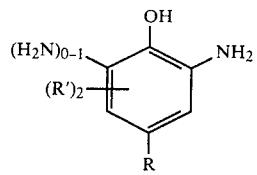

Formula II wherein R is derived from homopolymerized or interpolymerized C₂₋₁₀ 1-olefins and has an average of from about 30 to about 750 aliphatic carbon atoms; R' is selected from the group consisting of lower alkyl, lower alkoxyl, nitro and halo; and z is 0 or 1, with the proviso that when there is only one amino group ortho to the phenolic hydroxyl group, then R', if present, can be ortho to said hydroxyl group. In this embodiment, R often contains an average of at least 50 aliphatic carbon atoms and is made from homo- and inter-polymers of ethylene, propylene, butenes and mixtures thereof. R groups derived from polymerized isobutene are typical.

In a presently especially preferred embodiment of the invention which is within the embodiment represented by Formula II, R' is nitro, z is 0 or 1 with the proviso that if z is 1 then there is only one amino group ortho to the phenolic hydroxyl group and the R' is also ortho to said hydroxyl group. In this especially preferred embodiment, the preferences for R discussed hereinbefore apply.

The amino phenols of this invention are conveniently made by alkylating a phenol with an olefinic alkylating agent to form an alkylated phenol. This alkylated phenol is nitrated to form an intermediate nitro phenol which is converted to the desired amino phenol by reducing at least some of the nitro groups to amino groups.

Techniques for alkylating phenols are well known to those skilled in the art as the above-noted article in Kirk-Othmer "Encyclopedia of Chemical Technology" demonstrates. Techniques for nitrating phenols are also known. See, for example, in Kirk-Othmer "Encyclopedia of Chemical Technology", Second Edition, Vol. 13, the article entitled "Nitrophenols", page 888 et seq., as well as the treatises "Aromatic Substitution, Nitration and Halogenation" by P. B. D. De La Mare and J. H. Ridd, N.Y., Academic Press, 1959; "Nitration and Aromatic Reactivity" by J. G. Hogget, London, Cambridge University Press, 1961; and "The Chemistry of the Nitro and Nitroso Groups", Henry Feuer, Editor, Interscience Publishers, N.Y., 1969.

Phenols can be nitrated with nitric acid, mixtures of nitric acid with acids such as sulfuric acid or boron trifluoride, nitrogen tetraoxide, nitronium tetrafluoroborates and acyl nitrates. Generally, nitric acid of a concentration of, for example, about 30-90% is a convenient nitrating reagent. Substantially inert liquid diluents and solvents such as acetic or butyric acid can aid in carrying out the reaction by improving reagent contact.

Conditions and concentrations for nitrating phenols are also well known in the art. For example, the reaction can be carried out at temperatures of about −15° C. to about 150° C. Usually nitration is conveniently carried out between about 25°–75° C.

Generally, depending on the particular nitrating agent, about 0.5–4 moles of nitrating agent is used for every mole of phenol intermediate to be nitrated. When nitric acid is used as a nitrating agent usually about 1.0 to about 3.0 moles per mole of phenol intermediate is used. Up to about a 5 molar excess of nitrating agent (per mole of phenol intermediate) may be used when it is desired to drive the reaction forward or carry it out rapidly.

Nitration of a phenol intermediate generally takes 0.25 to 24 hours, though it may be convenient to react the nitration mixture for longer periods, such as 96 hours.

Reduction of aromatic nitro compounds to the corresponding amines is also well known. See, for example, the article entitled "Amination by Reduction" in Kirk-Othmer "Encyclopedia of Chemical Technology", Second Edition, Vol. 2, pages 76–99. Generally, such reductions can be carried out with, for example, hydrogen, carbon monoxide or hydrazine, (or mixtures of same) in the presence of metallic catalysts such as palladium, platinum and their oxides, nickel, copper chromite, etc. Co-catalysts such as alkali or alkaline earth metal hydroxides or amines (including amino phenols) can be used in these catalyzed reductions Reduction can also be accomplished through the use of reducing metals in the presence of acids, such as hydrochloric acid. Typical reducing metals are zinc, iron and tin; salts of these metals can also be used.

Nitro groups can also be reduced in the Zinin reaction, which is discussed in "Organic Reactions", Vol. 20, John Wiley & Sons, N.Y., 1973, page 445 et seq. Generally, the Zinin reaction involves reduction of a nitro group with divalent negative sulfur compounds, such as alkali metal sulfides, polysulfides and hydrosulfides.

The nitro groups can be reduced by electrolytic action; see, for example, the "Amination by Reduction" article, referred to above.

Typically the amino phenols of this invention are obtained by reduction of nitro phenols with hydrogen in the presence of a metallic catalyst such as discussed above. This reduction is generally carried out at temperatures of about 15°–250° C., typically, about 50°–150° C., and hydrogen pressures of about 0–2000 psig, typically, about 50–250 psig. The reaction time for reduction usually varies between about 0.5–50 hours. Substantially inert organic liquid diluents and solvents, such as ethanol, cyclohexane, etc., can be used to facilitate the reaction. The amino phenols can be isolated from the reduction reaction mixture by well-known techniques such as distillation, filtration, extraction, and so forth. However, it should be understood that it is not necessary to obtain the amino phenols in a pure condition for them to be useful. For example, the presence of some unreduced nitro phenol intermediates in the amino phenols does not prevent the amino phenols from being advantageously used as lubricant and fuel additives. Similarly, the presence of reaction solvents and diluents does not destroy the usefulness of the amino phenol. Generally, any material in the reaction mixture which cannot be readily removed by conventional distillation and/or filtration techniques will not be removed for economic reasons.

The reduction is carried out until at least about 50%, usually about 80%, of the nitro groups present in the nitro intermediate mixture are converted to amino groups. The typical route to the amino phenols of this invention just described can be summarized as (I) nitrating with at least one nitrating agent at least one compound of the formula

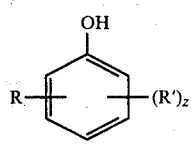

wherein R is a substantially saturated hydrocarbyl group of about 30 to about 750 aliphatic carbon atoms; R' is a substituent selected from the group consisting of lower alkyl, lower alkoxyl, nitro and halo; z is 0 or 1; to form a first reaction mixture containing a nitro intermediate, and (II) reducing at least about 50% of the nitro groups in said first reaction mixture to amino groups. Usually the nitrating agent is nitric acid and the reduction is carried out with hydrogen in the presence of a metallic hydrogenation catalyst.

The following examples demonstrate the practice of the present invention in some of its various aspects. All parts and percentages in the examples and elsewhere in the specification and claims are by weight and likewise, all temperatures are in degrees centigrade (°C.), unless expressly stated to the contrary.

EXAMPLE 1A

To a mixture of 361.2 parts of a deca(propylene)-substituted phenol and 270.9 parts of glacial acetic acid, at 7°–17°, is added a mixture of 90.3 parts of nitric acid (70–71% $HNO_3$) and 90.3 parts of glacial acetic acid. The addition is carried out over 1.5 hours while the reaction mixture is cooled externally to keep it at 7°–17°. The cooling bath is removed and the reaction stirred for 2 hours at room temperature. The reaction is then stripped at 134°/35 torr and filtered to provide the desired nitrated intermediate as a filtrate having a nitrogen content of 4.65%.

EXAMPLE 1B

A mixture of 150 parts of the product of 1A and 50 parts of ethanol is added to an autoclave. This mixture is degassed by purging with nitrogen and 0.75 part of palladium on charcoal catalyst is added. The autoclave is evacuated and pressured with nitrogen several times and then put under a hydrogen pressure of 100 psig. The reaction mixture is kept at 95 to 100° for 2.5 hours while the hydrogen pressure varies from 100 to 20 psig. As the hydrogen pressure drops below 30 psig, it is adjusted back to 100 psig. The reaction is continued for 20.5 hours at which point the autoclave is reopened and an additional 0.5 part of palladium on charcoal catalyst added. After repeated nitrogen purging (3 times) the autoclave is again pressured to 100 psig with hydrogen and the reaction continued for an additional 16.5 hours. A total of 2.0 moles of hydrogen is fed to the autoclave. The reaction mixture is filtered and stripped to 130°/16 torr. A second filtration provides the amino phenol product as a filtrate which is predominantly a monoamine product having the amino group ortho to the hydroxyl group and the deca(propylene) substituent para to the hydroxyl group.

EXAMPLE 2A

To a mixture of 3,685 parts of a polybutene-substituted phenol (wherein the polybutene substituent contains 40 to 45 carbon atoms) and 1,400 parts of textile spirits is added 790 parts of nitric acid (70%). The reaction temperature is kept below 50°. After being stirred for about 0.7 hour, the reaction mixture is poured into 5,000 parts of ice and stored for 16 hours. The organic layer which separates is washed twice with water and then combined with 1,000 parts of benzene. This solution is stripped to 170° and the residue filtered to provide the desired intermediate as a filtrate.

EXAMPLE 2B

A mixture of 130 parts of the product of 2A, 130 parts of ethanol, and 0.2 part of platinum oxide (86.4% $PtO_2$) is charged to a hydrogenation bomb. The bomb is purged several times with hydrogen and then charged to 54 psig with hydrogen. The bomb is rocked for 24 hours and again charged to 70 psig with hydrogen. Rocking is continued for an additional 98 hours. Stripping of the resulting reaction mixture to 145°/760 torr provides the desired amino phenol product as a semi-solid residue.

EXAMPLE 2C

A mixture of 420 parts of the product of 2A, 326 parts of ethanol and 12 parts of commercial nickel on kieselguhr catalyst is charged to an appropriately sized hydrogenation bomb. The bomb is pressured to 1,480 psig with hydrogen and agitated for 5.25 hours. The resultant reaction mixture is stripped to 65°/30 torr to provide the amino phenol product as a semi-solid residue.

EXAMPLE 2D

A mixture of 105 parts of the product of 2A, 303 parts cyclohexane and 4 parts commercial Raney nickel catalyst is charged to an appropriately sized hydrogenation bomb. The bomb is pressured to 1,000 psig with hydrogen and agitated at about 50° for 16 hours. The bomb is again pressured to 1,100 psig and agitated for another 24 hours. The bomb is then opened and the reaction mixture filtered and recharged to the bomb with a fresh portion of 4 parts of Raney nickel catalyst. The bomb is pressured to 1,100 psig and agitated for 24 hours. The resultant reaction mixture is stripped to 95°/28 torr to provide the amino phenol product as a semi-solid residue.

EXAMPLE 3A

An alkylated phenol is prepared by reacting phenol with polybutene having a number average molecular weight of approximately 1000 (vapor phase osmometry) in the presence of a boron trifluoride-phenol complex catalyst. Stripping of the product thus formed first to 230°/760 torr and then to 205°/50 torr (vapor temperatures) provides the desired alkylated phenol.

To a mixture of 265 parts of the alkylated phenol, 176 parts blend oil and 42 parts of a petroleum naphtha having a boiling point of approximately 20° is added slowly to a mixture of 18.4 parts of concentrated nitric acid (69-70%) and 35 parts of water. The reaction mixture is stirred for 3 hours at about 30°-45°, stripped to 120°/20 torr and filtered to provide as the filtrate an oil solution of the desired nitro phenol intermediate.

EXAMPLE 3B

A mixture of 1,500 parts of the product solution of 3A, 642 parts of isopropanol and 7.5 parts of nickel on kieselguhr catalyst is charged to an autoclave under a nitrogen atmosphere. After purging and evacuation with nitrogen three times, the autoclave is pressured to 100 psig with hydrogen and stirring is begun. The reaction mixture is held at 96° for a total of 14.5 hours while a total of 1.66 moles of hydrogen is fed to it. After purging with nitrogen three times, the reaction mixture is filtered and the filtrate stripped to 120°/18 torr. Filtration provides the desired amino phenol product in an oil solution.

EXAMPLE 4A

To a mixture of 400 parts of polybutene-substituted phenol (wherein the polybutene substituent contains approximately 100 carbon atoms), 125 parts of textile spirits and 266 parts of a diluent mineral oil at 28° is slowly added 22.83 parts of nitric acid (70%) in 50 parts of water over a period of 0.33 hour. The mixture is stirred at 28°–34° for 2 hours and stripped to 158°/30 torr, filtration provides an oil solution (40%) of the desired nitro phenol intermediate having a nitrogen content of 0.88%.

EXAMPLE 4B

A mixture of 93 parts of the product solution of Example 4A and 93 parts of a mixture of toluene and isopropanol (50/50 by weight) is charged to an appropriately sized hydrogenation vessel. The mixture is degassed and nitrogen purged; 0.31 part of a commercial platinum oxide catalyst (86.4% $PtO_2$) is added. The reaction vessel is pressured to 57 psig and held at 50°–60° for 21 hours. A total of 0.6 mole of hydrogen is fed to the reaction vessel. The reaction mixture is then filtered and the filtrate stripped to yield the desired amino phenol product in an oil solution containing 0.44% nitrogen.

EXAMPLE 5A

To a mixture of 654 parts of the polybutene-substituted phenol of Example 3A and 654 parts of isobutyric acid at 27° to 31°, is added 90 parts of 16 molar nitric acid over a period of 0.5 hour. The reaction mixture is held at 50° for 3 hours and then stored at room temperature for 63 hours. Stripping to 160°/26 torr and filtration through filter aid provides the desired dinitro intermediate.

EXAMPLE 5B

A mixture of 600 parts of the product of 5A, 257 parts of isopropanol and 3.0 parts of nickel on kieselguhr catalyst is charged to an autoclave under a nitrogen atmosphere. After purging and evacuation with nitrogen three times, the autoclave is pressured to 100 psig with hydrogen and stirring is begun. The reaction mixture is held at 96° for a total of 14.5 hours while a total of 1.66 moles of hydrogen is fed to it. After purging with nitrogen three times, the reaction mixture is filtered and the filtrate stripped to 120°/18 torr. Filtration provides the desired product in an oil solution.

As previously indicated, the amino phenols of this invention are useful as additives in lubricant compositions where they function primarily as detergents and dispersants. They are particularly useful where the oil is subjected to high temperature environments or to cyclic stresses such as those encountered in on-and-off engine operation.

The lubricating oil compositions of this invention are based on natural and synthetic lubricating oils and mixtures thereof. These lubricants include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants, hydraulic fluids and other lubricating oil and grease compositions can also benefit from the incorporation therein of the amino phenols of the present invention.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide homopolymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitble class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butylphenyl)silicate, hexyl-(4-methyl-2-pentoxy)-disiloxane, poly(methyl)siloxanes, poly(methylphenyl)siloxanes, etc.). Other synthetic lubricating oils include liquid esters of phosphorous-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

In general, about 0.05–30, usually about 0.1–15 parts (by weight) of at least one amino phenol of this invention is dissolved or stably dispersed in 100 parts of oil to produce a satisfactory lubricant. The invention also contemplates the use of other additives in combination with the composition of this invention. Such additives include, for example, auxiliary detergents and dispersants of the ash-producing or ashless type, oxidation-inhibiting agents, pour point depressing agents, extreme pressure agents, color stabilizers and anti-foam agents.

The amino phenols of this invention can also be used in fuels where they function as detergent dispersants, anti-oxidants and anti-corrosion agents. Fuel compositions of this invention usually contain a major portion of a normally liquid fuel such as hydrocarbonaceous petroleum distillate fuel (e.g., motor gasoline as defined by ASTM Specification D-439-73 and diesel fuel or fuel oil as defined by ASTM Specification D-396). Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Generally, these fuel compositions contain an amount of at least one amino phenol of this invention sufficient to impart anti-oxidant and/or dispersant and detergent properties to the fuel; usually this amounts is about 1 to about 10,000, preferably 4 to 1,000, parts by weight of the reaction product per million parts by weight of fuel.

The preferred gasoline-based fuel compositions generally exhibit excellent engine oil sludge dispersancy and detergency properties. In addition, they resist oxidation.

The fuel compositions of this invention can contain, in addition to the compositions of this invention, other additives which are well known to those of skill in the art. These can include anti-knock agents such as tetraalkyl lead compounds, lead scavengers such as haloalkanes (e.g., ethylene dichloride and ethylene dibromide), deposit preventors or modifiers such as triaryl phosphates, dyes, cetane improvers, anti-oxidants such as 2,6-di-tertiarybutyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described compositions of this invention are combined with other ashless dispersants in gasoline. Such ashless dispersants are preferably esters of a mono- or polyol and a high molecular weight mono- or poly- carboxylic acid acylating agent containing at least 30 carbon atoms in the acyl moiety. Such esters are well known to those of skill in the art. See, for example, French Pat. No. 1,396,645, British Pat. Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification No. 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0; preferably about 1 to about 10 parts of composition of this invention to 1 part ashless dispersant.

In still another embodiment of this invention, the inventive amino phenols can be combined with Mannich condensation products formed from substituted phenols, aldehydes, polyamines, and amino pyridines to make lubricants and/or fuel additives. Such condensation products are described in U.S. Pat. Nos. 3,649,659; 3,558,743; 3,539,633; 3,704,308; and 3,725,277.

The amino phenols of this invention can be added directly to the fuel or lubricating oil to form the fuel and lubricant compositions of this invention or they can be diluted with at least one substantially inert, normally liquid organic solvent/diluent such as mineral oil, xylene, or a normally liquid fuel as described above, to form an additive package which is then added to the fuel or lubricating oil in sufficient amounts to form the inventive fuel and lubricant composition described herein. These concentrates generally contain about 30 to about 90 percent of the composition of this invention and can contain in addition any of the above-described conventional additives, particularly the afore-described ashless dispersants in the aforesaid proportions. The remainder of the concentrate is the solvent/diluent.

What is claimed is:

1. An amino phenol of the formula

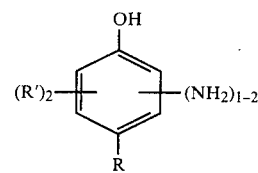

wherein R is a substantially saturated hydrocarbyl substituent having an average of from about 30 to about 750 aliphatic carbon atoms; group R' is a substituent selected from the group consisting of lower alkyl, lower alkoxyl, nitro, and halo; and z is 0 or 1.

2. An amino phenol as claimed in claim 1 wherein R contains at least about 50 aliphatic carbon atoms.

3. An amino phenol as claimed in claim 1 wherein R is an alkyl or alkenyl group.

4. An amino phenol as claimed in claim 3 wherein z is 0.

5. An amino phenol as claimed in claim 4 wherein R contains at least 50 carbon atoms.

6. An amino phenol as claimed in claim 1 wherein R is a substituent derived from homopolymerized or interpolymerized $C_{2-10}$ olefins.

7. An amino phenol as claimed in claim 6 wherein said $C_{2-10}$ olefins are selected from the group consisting of $C_{2-10}$ 1-olefins and mixtures thereof.

8. An amino phenol as claimed in claim 7 wherein said 1-olefins are selected from the group consisting of ethylene, propylene, butenes, and mixtures thereof.

9. An amino phenol of the formula

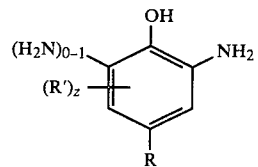

wherein R is derived from homopolymerized or interpolymerized $C_{2-10}$ 1-olefins and has an average of from about 30 to about 750 aliphatic carbon atoms; R' is selected from the group consisting of lower alkyl, lower alkoxyl, nitro, and halo; and z is 0 or 1, with the proviso that when there is only one amino group ortho to the phenolic hydroxyl group, then R', if present, can be ortho to said hydroxyl group.

10. An amino phenol as claimed in claim 9 wherein said 1-olefins are selected from the group consisting of ethylene, propylenes, butenes and mixtures thereof.

11. An amino phenol as claimed in claim 10 wherein R is derived from polymerized isobutene.

12. An amino phenol as claimed in claim 11 wherein R contains an average of at least about 50 aliphatic carbon atoms.

13. An amino phenol as claimed in claim 12 wherein z is 0.

14. An amino phenol as claimed in claim 9 wherein R' is nitro, z is 0 or 1, with the proviso that if z is 1, then there is only one amino group ortho to the phenolic hydroxyl group and R' is also ortho to said hydroxyl group.

15. An amino phenol as claimed in claim 14 wherein said 1-olefins are selected from the group consisting of ethylene, propylenes, butenes and mixtures thereof.

16. An amino phenol as claimed in claim 15 wherein R is derived from polymerized isobutene.

17. An amino phenol as claimed in claim 16 wherein R contains an average of at least about 50 aliphatic carbon atoms.

18. An amino-containing composition made by
(I) nitrating with at least one nitrating agent at least one compound of the formula

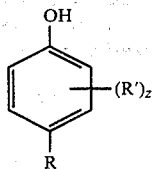

wherein R is a substantially saturated hydrocarbyl group of about 30 to about 750 aliphatic carbon atoms; R' is a substituent selected from the group consisting of lower alkyl, lower alkoxyl, nitro and halo; z is 0 or 1; to form a first reaction mixture containing a nitro intermediate, and (II) reducing at least about 50% of the nitro groups in said first reaction mixture to amino groups.

19. An amino-containing composition as claimed in claim 18 wherein R is an alkyl or alkenyl group.

20. An amino-containing composition as claimed in claim 19 wherein z is 0.

21. An amino-containing composition as claimed in claim 18 wherein R has an average of at least about 50 carbon atoms and is derived from homopolymerized or interpolymerized $C_{2-10}$ olefins.

22. An amino-containing composition as claimed in claim 18 wherein the nitrating agent is nitric acid.

23. An amino-containing composition as claimed in claim 22 wherein the nitro intermediate is reduced by hydrogen in the presence of a metallic hydrogenation catalyst.

24. An amino-containing composition as claimed in claim 18 wherein R is derived from polymerized isobutene and z is 0.

25. A lubricant composition other than a two-cycle engine oil containing a major proportion of a lubricating oil of lubricating viscosity and about 0.05–30 parts by weight per 100 parts by weight of said oil of at least one amino phenol as described in claim 1.

26. A lubricant composition other than a two-cycle engine oil containing a major proportion of a lubricating oil of lubricating viscosity and about 0.05–30 parts by weight per 100 parts by weight of said oil of at least one amino phenol as claimed in claim 4.

27. A lubricant composition other than a two-cycle engine oil containing a major proportion of a lubricating oil of lubricating viscosity and about 0.05–30 parts by weight per 100 parts by weight of said oil of at least one amino phenol as claimed in claim 8.

28. A lubricant composition other than a two-cycle engine oil containing a major proportion of a lubricating oil of lubricating viscosity and about 0.05–30 parts by weight per 100 parts by weight of said oil of at least one amino phenol as claimed in claim 9.

29. A lubricant composition other than a two-cycle engine oil containing a major proportion of a lubricating oil of lubricating viscosity and about 0.05–30 parts by weight per 100 parts by weight of said oil of at least one amino phenol as claimed in claim 14.

30. A lubricant composition other than a two-cycle engine oil containing a major proportion of a lubricating oil of lubricating viscosity and about 0.05–30 parts by weight per 100 parts by weight of said oil of at least one amino-containing composition as claimed in claim 18.

31. A lubricant composition other than a two-cycle engine oil containing a major proportion of a lubricating oil of lubricating viscosity and about 0.05–30 parts by weight per 100 parts by weight of said oil of at least one amino-containing composition as claimed in claim 23.

32. A lubricant composition other than a two-cycle engine oil containing a major proportion of a lubricating oil of lubricating viscosity and about 0.05–30 parts by weight per 100 parts by weight of said oil of at least one amino-containing composition as claimed in claim 24.

33. An additive concentrate for use in normally liquid fuels or lubricating oils of lubricating viscosity comprising a substantially inert solvent/diluent and about 30–90% of at least one amino phenol as described in claim 1.

34. An additive concentrate for use in normally liquid fuels or lubricating oils of lubricating viscosity comprising a substantially inert solvent/diluent and about 30–90% of at least one amino phenol as described in claim 4.

35. An additive concentrate for use in normally liquid fuels or lubricating oils of lubricating viscosity comprising a substantially inert solvent/diluent and about 30–90% of at least one amino phenol as described in claim 8.

36. An additive concentrate for use in normally liquid fuels or lubricating oils of lubricating viscosity comprising a substantially inert solvent/diluent and about 30–90% of at least one amino phenol as described in claim 9.

37. An additive concentrate for use in normally liquid fuels or lubricating oils of lubricating viscosity comprising a substantially inert solvent/diluent and about 30–90% of at least one amino phenol as described in claim 14.

38. An additive concentrate for use in normally liquid fuels or lubricating oils of lubricating viscosity comprising a substantially inert solvent/diluent and about 30–90% of at least one amino-containing composition as described in claim 18.

39. An additive concentrate for use in normally liquid fuels or lubricating oils of lubricating viscosity comprising a substantially inert solvent/diluent and about 30–90% of at least one amino-containing composition as described in claim 23.

40. An additive concentrate for use in normally liquid fuels or lubricating oils of lubricating viscosity comprising a substantially inert solvent/diluent and about 30–90% of at least one amino-containing composition as described in claim 24.

41. A fuel composition containing a major proportion of a normally liquid fuel and about 1 to about 10,000 parts by weight per million parts by weight of fuel of at least one amino phenol as described in claim 1.

42. A fuel composition containing a major proportion of a normally liquid fuel and about 1 to about 10,000 parts by weight per million parts by weight of fuel of at least one amino phenol as claimed in claim 4.

43. A fuel composition containing a major proportion of a normally liquid fuel and about 1 to about 10,000 parts by weight per million parts by weight of fuel of at least one amino phenol as claimed in claim 8.

44. A fuel composition containing a major proportion of a normally liquid fuel and about 1 to about 10,000 parts by weight per million parts by weight of fuel of at least one amino phenol as claimed in claim 9.

45. A fuel composition containing a major proportion of a normally liquid fuel and about 1 to about 10,000 parts by weight per million parts by weight of fuel of at least one amino phenol as claimed in claim 14.

46. A fuel composition containing a major proportion of a normally liquid fuel and about 1 to about 10,000 parts by weight per million parts by weight of fuel of at least one amino-containing composition as claimed in claim 18.

47. A fuel composition containing a major proportion of a normally liquid fuel and about 1 to about 10,000 parts by weight per million parts by weight of fuel of at least one amino-containing composition as claimed in claim 23.

48. A fuel composition containing a major proportion of a normally liquid fuel and about 1 to about 10,000 parts by weight per million parts by weight of fuel of at least one amino-containing composition as claimed in claim 24.

* * * * *

UNITED STATES PATENT AND TRADEMARK OFFICE
CERTIFICATE OF CORRECTION

PATENT NO. : 4,320,020
DATED : March 16, 1982
INVENTOR(S) : Richard Michael Lange It is certified that error appears in the above—identified patent and that said Letters Patent is hereby corrected as shown below:

Column 12, line 5, the subscript "2" for R' should be --z--.

Signed and Sealed this

Twenty-ninth Day of June 1982

[SEAL]

Attest:

GERALD J. MOSSINGHOFF

*Attesting Officer*     *Commissioner of Patents and Trademarks*